US00RE36268E

United States Patent [19]

Szuminsky et al.

[11] E Patent Number: Re. 36,268

[45] Reissued Date of Patent: Aug. 17, 1999

[54] METHOD AND APPARATUS FOR AMPEROMETRIC DIAGNOSTIC ANALYSIS

[75] Inventors: Neil J. Szuminsky, Pittsburgh; Joseph Jordan, deceased, late of State College, by Colina L. Jordan, executrix; Paul A. Pottgen, Allison Park; Jonathan L. Talbott, Freedom, all of Pa.

[73] Assignee: Boehringer Mannheim Corporation, Indianapolis, Ind.

[21] Appl. No.: 08/679,312

[22] Filed: Jul. 12, 1996

Related U.S. Patent Documents

Reissue of:

[64] Patent No.: 5,108,564
Issued: Apr. 28, 1992
Appl. No.: 08/745,544
Filed: Aug. 15, 1991

[60] Continuation of application No. 08/176,863, Dec. 30, 1993, abandoned, which is a division of application No. 07/322,598, Mar. 13, 1989, Pat. No. 5,128,015, which is a continuation-in-part of application No. 07/168,295, Mar. 15, 1988, abandoned.

[51] Int. Cl.[6] ..... G01N 27/26

[52] U.S. Cl. ..... 205/777.5; 205/782.5; 204/412; 204/415; 435/287.1; 435/289.1; 435/817

[58] Field of Search ..... 204/403, 415, 204/412; 205/777.5, 782.5; 435/287.1, 289.1, 817

[56] References Cited

U.S. PATENT DOCUMENTS 3,838,033 9/1974 Mindt et al. ..... 204/195 B
3,925,183 12/1975 Oswin et al. ..... 204/195 R (List continued on next page.)

FOREIGN PATENT DOCUMENTS

0078590A1 5/1983 European Pat. Off. .
0078636B1 5/1983 European Pat. Off. .
0125137B1 11/1984 European Pat. Off. .
0127958B1 12/1984 European Pat. Off. .
0136362 4/1985 European Pat. Off. .

(List continued on next page.)

OTHER PUBLICATIONS

Van Nostrand Reinhold Encyclopedia of Chemistry; pp. 149–150 (4th edition 1984) no month available.

Biochemica Information; pp. 18, 19, 27 and 28 (J. Keesey, ed., Boehringer Mannheim Biochemicals, 1987) no month available.

Laboratory Techniques in Electroanalytical Chemistry; pp. 51–64 and 124 (Kissinger and Heineman, eds., 1984) no month available.

Talbott et al.; "A New Microchemical Approach to Amperometric Analysis", Feb. 1988, vol. 37, pp. 5–12, Microchemical Journal.

Tokuda, Koichi; "Measurement of Current—Potential Curves"; 1986; pp. 471–475; Denki Kagaku (English Translation Included) no month available.

Myland, Janice C. and Oldham, Keith B.; "Membrane–Covered Oxygen Sensors: An Exact Treatment of the Switch–on Transient"; Aug. 1984; pp. 1815–1823; J. Electrochem. Soc.

Williams et al.; "Electrochemical—Enzymatic Analysis of Blood Glucose and Lactate"; Jan. 1970; pp. 118–121; Analytical Chemistry.

Talbott, Jonathan Lee; "Enzymatic Amperometry of Glucose"; 1988; Pennsylvania State University (Thesis for Doctor of Philosophy in Chemistry) no month available.

*Primary Examiner*—Bruce F. Bell
*Attorney, Agent, or Firm*—D. Michael Young

[57] ABSTRACT

The present invention relates to a novel method and apparatus for the amperometric determination of an analyte, and in particular, to an apparatus for amperometric analysis utilizing a novel disposable electroanalytical cell for the quantitative determination of biologically important compounds from body fluids.

44 Claims, 6 Drawing Sheets

U.S. PATENT DOCUMENTS

| | | | |
|---|---|---|---|
| 4,005,002 | 1/1977 | Racine et al. | 204/195 P |
| 4,169,779 | 10/1979 | Tataria et al. | 204/195 P |
| 4,217,196 | 8/1980 | Huch | 204/195 B |
| 4,224,125 | 9/1980 | Nakamura et al. | 204/195 B |
| 4,225,410 | 9/1980 | Pace | 204/195 R |
| 4,321,123 | 3/1982 | Nakamura et al. | 204/195 B |
| 4,392,933 | 7/1983 | Nakamura et al. | 204/403 |
| 4,407,959 | 10/1983 | Tsuji et al. | 435/288 |
| 4,420,564 | 12/1983 | Tsuji et al. | 435/288 |
| 4,431,507 | 2/1984 | Nankai et al. | 204/403 |
| 4,545,382 | 10/1985 | Higgins et al. | 128/635 |
| 4,579,643 | 4/1986 | Mase et al. | 204/427 |
| 4,654,197 | 3/1987 | Lilja et al. | 422/56 |
| 4,655,901 | 4/1987 | Mase et al. | 204/426 |
| 4,682,602 | 7/1987 | Prohaska | 128/635 |
| 4,711,245 | 12/1987 | Higgins et al. | 128/635 |
| 4,758,323 | 7/1988 | Davis et al. | 204/403 |
| 4,796,014 | 1/1989 | Chia | 340/573 |
| 4,810,633 | 3/1989 | Bauer et al. | 435/25 |
| 4,820,399 | 4/1989 | Senda et al. | 204/403 |
| 4,820,636 | 4/1989 | Hill et al. | 435/14 |
| 4,830,959 | 5/1989 | McNeil et al. | 435/7 |
| 4,836,904 | 6/1989 | Armstrong et al. | 204/294 |
| 4,894,137 | 1/1990 | Takizawa et al. | 204/403 |
| 4,897,173 | 1/1990 | Nankai et al. | 204/403 |
| 4,927,516 | 5/1990 | Yamaguchi et al. | 204/403 |
| 4,935,105 | 6/1990 | Churchouse | 204/153.12 |
| 4,935,106 | 6/1990 | Liston et al. | 204/153.1 |
| 4,938,860 | 7/1990 | Wogoman | 204/403 |
| 4,948,727 | 8/1990 | Cass et al. | 435/18 |
| 4,952,300 | 8/1990 | Diamond | 204/406 |
| 4,959,305 | 9/1990 | Woodrum | 435/7 |
| 4,970,145 | 11/1990 | Bennetto et al. | 435/14 |
| 4,995,402 | 2/1991 | Smith et al. | 128/771 |
| 5,030,310 | 7/1991 | Wogoman | 156/252 |
| 5,049,487 | 9/1991 | Phillips et al. | 435/4 |
| 5,140,393 | 8/1992 | Hijikihigawa et al. | 357/25 |
| 5,141,868 | 8/1992 | Shanks et al. | 435/288 |
| 5,171,689 | 12/1992 | Kawaguri et al. | 435/290 |

FOREIGN PATENT DOCUMENTS

| | | |
|---|---|---|
| 0136362B1 | 4/1985 | European Pat. Off. . |
| 0170375B1 | 2/1986 | European Pat. Off. . |
| 0177743B1 | 4/1986 | European Pat. Off. . |
| 0206218A2 | 12/1986 | European Pat. Off. . |
| 0230472 | 8/1987 | European Pat. Off. . |
| 0230472A1 | 8/1987 | European Pat. Off. . |
| 0230786A1 | 8/1987 | European Pat. Off. . |
| 0241309A3 | 10/1987 | European Pat. Off. . |
| 0255291A1 | 2/1988 | European Pat. Off. . |
| 55-10584 | 1/1980 | Japan . |
| 57-98853 | 6/1982 | Japan . |
| 59-166852 | 9/1984 | Japan . |
| 60-173457 | 9/1985 | Japan . |
| 60-173458 | 9/1985 | Japan . |
| 60-173459 | 9/1985 | Japan . |
| 60-211350 | 10/1985 | Japan . |
| 61-90050 | 5/1986 | Japan . |
| 61-91558 | 5/1986 | Japan . |
| 61-294356 | 12/1986 | Japan . |
| 62-156553 | 7/1987 | Japan . |
| 63-3249 | 1/1988 | Japan . |
| 63-58149 | 3/1988 | Japan . |
| 63-128252 | 5/1988 | Japan . |
| 2154003 | 8/1985 | United Kingdom . |
| WO86/04926 | 8/1986 | WIPO . |
| WO86/07632 | 12/1986 | WIPO . |

METHOD AND APPARATUS FOR AMPEROMETRIC DIAGNOSTIC ANALYSIS

Matter enclosed in heavy brackets [ ] appears in the original patent but forms no part of this reissue specification; matter printed in italics indicates the additions made by reissue.

The present application *is a continuation of Ser. No. 08/176,863 filed Dec. 30, 1993, now abandoned; which is a Re-issue of Ser. No. 07/745,544 filed Aug. 15, 1991, now U.S. Pat. No. 5,108,564 which* is a division of application Ser. No. 07/322,598, filed Mar. 13, 1989, which is a continuation-in-part of our earlier filed application, U.S. Ser. No. 168,295, filed Mar. 15, 1988, *now abandoned.*

FIELD OF THE INVENTION

The present invention relates to a disposable electroanalytical cell and a method and apparatus for quantitatively determining the presence of biologically important compounds such as glucose; TSH; T4; hormones such as HCG; cardiac glycosides such as Digoxin; antiarrhythmics such as Lidocaine; antiepileptics such as phenobarbital; antibiotics such as Gentamicin; cholesterol; non-therapeutic drugs and the like from body fluids.

Although the present invention has broad applications, for purposes of illustration of the invention specific emphasis will be placed upon its application in quantitatively determining the presence of two biologically important compounds—glucose and cholesterol.

WITH RESPECT TO GLUCOSE

Diabetes, and specifically diabetes mellitus, is a metabolic disease characterized by deficient insulin production by the pancreas which results in abnormal levels of blood glucose. Although this disease afflicts only approximately 4% of the population in the United States, it is the third leading cause of death following heart disease and cancer. With proper maintenance of the patient's blood sugar through daily injections of insulin, and strict control of dietary intake, the prognosis for diabetics is excellent. However, the blood glucose levels must be closely followed in the patient either by clinical laboratory analysis or by daily analyses which the patient can conduct using relatively simple, non-technical, methods.

At the present, current technology for monitoring blood glucose is based upon visual or instrumental determination of color change produced by enzymatic reactions on a dry reagent pad on a small plastic strip. These colorimetric methods which utilize the natural oxidant of glucose to gluconic acid, specifically oxygen, are based upon the reactions:

$$\text{B-D-Glucose}+O_2+H_2O \rightarrow \text{D-Gluconic Acid}+H_2O_2$$

$$H_2O_2+\text{Reagent-}H_2O+\text{color.}$$

WITH RESPECT TO CHOLESTEROL

Current technology for the determination of cholesterol is also based upon similar methods. In the case of cholesterol, the methods presently used are based upon the generalized reactions:

$$\text{Cholesterol}+H_2O+O_2 \rightarrow \text{Cholestenone}+H_2O_2$$

$$H_2O_2+\text{Reagent} \rightarrow H_2O+\text{color.}$$

In all present techniques, Dioxygen is the only direct oxidant used with the enzyme cholesterol oxidase for the determination of both free and total cholesterol. Using conventional test methods, oxygen must diffuse into the sensor solution during use from the surrounding air in order to provide sufficient reagent for a complete reaction with the analyte cholesterol in undiluted serum and whole blood specimens.

In both instances, the presence of the substance is determined by quantifying, either colorometrically or otherwise, the presence of hydrogen peroxide. The present methods of detection may include direct measurement of the hydrogen peroxide produced by either spectroscopic or electrochemical means and indirect methods in which the hydrogen peroxide is reacted with various dyes, in the presence of the enzyme peroxidase, to produce a color that is monitored.

While relatively easy to use, these tests require consistent user technique in order to yield reproducible results. For example, these tests require the removal of blood from a reagent pad at specified and critical time intervals. After the time interval, excess blood must be removed by washing and blotting, or by blotting alone, since the color measurement is taken at the top surface of the reagent pad. Color development is either read immediately or after a specified time interval.

These steps are dependent upon good and consistent operating technique requiring strict attention to timing. Moreover, even utilizing good operating technique, colorimetric methods for determining glucose, for example, have been shown to have poor precision and accuracy, particularly in the hypoglycemic range. Furthermore, instruments used for the quantitative colorimetric measurement vary widely in their calibration methods: some provide no user calibration while others provide secondary standards.

Because of the general lack of precision and standardization of the various methods and apparatus presently available to test for biologically important compounds in body fluids, some physicians are hesitant to use such equipment for monitoring levels or dosage. They are particularly hesitant in recommending such methods for use by the patients themselves. Accordingly, it is desirable to have a method and apparatus which will permit not only physician but patient self-testing of such compounds with greater reliability.

The present invention addresses the concerns of the physician by providing enzymatic amperometry methods and apparatus for monitoring compounds within whole blood, serum, and other body fluids. Enzymatic amperometry provides several advantages for controlling or eliminating operator dependant techniques as well as providing a greater linear dynamic range. A system based on this type of method could address the concerns of the physician hesitant to recommend self-testing for his patients.

Enzymatic amperometry methods have been applied to the laboratory based measurement of a number of analytes including glucose, blood urea nitrogen, and lactate. Traditionally the electrodes in these systems consist of bulk metal wires, cylinders or disks imbedded in an insulating material. The fabrication process results in individualistic characteristics for each electrode necessitating calibration of each sensor. These electrodes are also too costly for disposable use, necessitating meticulous attention to electrode maintenance for continued reliable use. This maintenance is not likely to be performed properly by untrained personnel (such as patients), therefore to be successful, an enzyme amperometry method intended for self-testing (or non-traditional site testing) must be based on a disposable sensor that can be produced in a manner that allows it to give reproducible output from sensor to sensor and at a cost well below that of traditional electrodes.

The present invention address these requirements by providing miniaturized disposable electroanalytic sample cells for precise micro-aliquote sampling, a self-contained, automatic means for measuring the electrochemical reduction of the sample, and a method for using the cell and apparatus according to the present invention.

The disposable cells according to the present invention are preferably laminated layers of metallized plastic and nonconducting material. The metallized layers provide the working and reference electrodes, the areas of which are reproducibly defined by the lamination process. An opening through these layers is designed to provide the sample-containing area or cell for the precise measurement of the sample. The insertion of the cell into the apparatus according to the present invention, automatically initiates the measurement cycle.

To better understand the process of measurement, a presently preferred embodiment of the invention is described which involves a two-step reaction sequence utilizing a chemical oxidation step using other oxidants than oxygen, and an electro-chemical reduction step suitable for quantifying the reaction production of the first step. One advantage to utilizing an oxidant other than dioxygen for the direct determination of an analyte is that they may be prepositioned in the sensor in a large excess of the analyte and thus ensure that the oxidant is not the limiting reagent (with dioxygen, there is normally insufficient oxidant initially present in the sensor solution for a quantitative conversion of the analyte).

In the oxidation reaction, a sample containing glucose, for example, is converted to gluconic acid and a reduction product of the oxidant. This chemical oxidation reaction has been found to precede to completion in the presence of an enzyme, glucose oxidase, which is highly specific for the substrate B-D-glucose, and catalyzes oxidations with single and double electron acceptors. It has been found, however, that the oxidation process does not proceed beyond the formation of gluconic acid, thus making this reaction particularly suited for the electrochemical measurement of glucose.

In a presently preferred embodiment, oxidations with one electron acceptor using ferricyanide, ferricinium, cobalt (III) [orthophenantroline] *orthophenanthroline*, and cobalt (III) dipyridyl are preferred. Benzoquinone is a two electron acceptor which also provides excellent electro-oxidation characteristics for amperometric quantitation.

Amperometric determination of glucose, for example, in accordance with the present invention utilizes Cottrell current micro-chronoamperometry in which glucose plus an oxidized electron acceptor produces gluconic acid and a reduced acceptor. This determination involves a preceding chemical oxidation step catalyzed by a bi-substrate bi-product enzymatic mechanism as will become apparent throughout this specification.

In this method of quantification, the measurement of a diffusion controlled current at an accurately specified time (e.g. 20, 30, or 50 seconds, for example) after the instant of application of a potential has the applicable equation for amperometry at a controlled potential (E=constant) of:

$$i(t) = nFAC_{metabolite}(D)^{0.5}(\pi t)^{-0.5}$$

where i denotes current, nF is the number of coulombs per mole, A[D] is the area of the electrode, D is the diffusion coefficient of the reduced form of the reagent, t is the preset time at which the current is measured, and C is the concentration of the metabolite. Measurements by the method according to the present invention of the current due to the reoxidation of the acceptors were found to be proportional to the glucose concentration in the sample.

The method and apparatus of the [prevent] *present* invention permit, in preferred embodiments, direct measurements of blood glucose, cholesterol and the like. Furthermore, the sample cell according to the [prevent] *present* invention, provides the testing of controlled volumes of blood without premeasuring. Insertion of the sample cell into the apparatus thus permits automatic functioning and timing of the reaction allowing for patient self-testing with a very high degree of precision and accuracy.

One of many of the presently preferred embodiments of the invention for use in measuring B-D glucose is described in detail to better understand the nature and scope of the invention. In particular, the method and apparatus according to this embodiment are designed to provide clinical self-monitoring of blood glucose levels by a diabetic patient. The sample cell of the invention is used to control the sampling volume and reaction media and acts as the electrochemical sensor. In this described embodiment, benzoquinone is used as the electron acceptor.

The basic chemical binary reaction utilized by the method according to the present invention is:

$$\text{B-D-glucose} + \text{Benzoquinone} + H_2O \rightarrow \text{Gluconic Acid} + \text{Hydroquinone}$$

$$\text{Hydroquinone} \rightarrow \text{benzoquinone} + 2e^- + 2H^+.$$

The first reaction is an oxidation reaction which proceeds to completion in the presence of the enzyme glucose oxidase. Electrochemical oxidation takes place in the second part of the reaction and provides the means for quantifying the amount of hydroquinone produced in the oxidation reaction. This holds true whether catalytic oxidation is conducted with two-electron acceptors or one electron acceptors such as ferricyanide (wherein the redox couple would be $Fe(CN)_6^{-3}/Fe(CN)_6^{-4}$), ferricinium, cobalt III [orthophenantroline] *orthophenanthroline* and cobalt (III) dipyridyl.

Catalytic oxidation by glucose oxidase is highly specific for B-D-glucose, but is nonselective as to the oxidant. It has now been discovered that the preferred oxidants described above have sufficiently positive potentials to convert substantially all of the B-D-glucose to gluconic acid. Furthermore, this system provides a means by which amounts as small a 1 mg of glucose (in the preferred embodiment) to 1000 mg of glucose can be measured per deciliter of sample—results which have not previously been obtained using other glucose self-testing systems.

The sensors containing the chemistry to perform the desired determination, constructed in accordance with the present invention, are used with a portable meter for self-testing systems. In use the sensor is inserted into the meter which turns the meter on and initiates a wait for the application of the sample. The meter recognizes sample application by the sudden charging current flow that occurs when the electrodes and the overlaying reagent layer are initially wetted by the sample fluid. Once the sample application is detected, the meter begins the reaction incubation step (the length of which is chemistry dependent) to allow the enzymatic reaction to reach completion. This period is on the order of 15 to 90 seconds for glucose, with incubation times of 20 to 45 seconds preferred. Following the incubation period, the instrument then imposes a known potential across the electrodes and measures the current at specific time points during the Cottrell current decay. Current measurements can be made in the range of 2 to 30 seconds following potential application with measurement times of 10 to 20 seconds preferred. These current values are then used to calculate the analyte concentration which is then displayed. The meter will then wait for either the user to remove the sensor or for a predetermined period before shutting itself down.

The present invention provides for a measurement system that eliminates several of the critical operator dependant variables that adversely affect the accuracy and reliability and provides for a greater dynamic range than other self-testing systems.

These and other advantages of the present invention will become apparent from a perusal of the following detailed description of one embodiment presently preferred for measuring glucose and another for measuring cholesterol which is to be taken in conjunction with the accompanying drawings in which like numerals indicate like components and in which.

Figure 1:
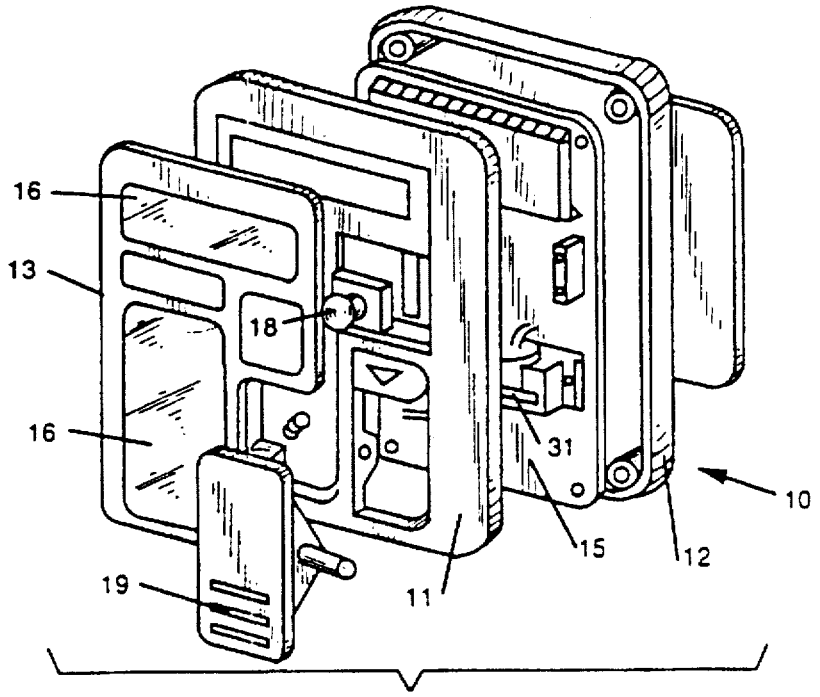
FIG. 1 is an exploded view of a portable testing apparatus according to the present invention.

With specific reference to FIG. 1, a portable electrochemical testing apparatus 10 is shown for use in patient self-testing, such as, for example, for blood glucose levels. Apparatus 10 comprises a front and back housing 11 and 12, respectively, a front panel 13 and a circuit board 15. Front panel 13 includes graphic display panels 16 for providing information and instructions to the patient, and direct read-out of the test results. While a start button 18 is provided to initiate an analysis, it is preferred that the system being operation when a sample cell 20 (FIG. 2) is inserted into the window 19 of the apparatus.

Figure 2:
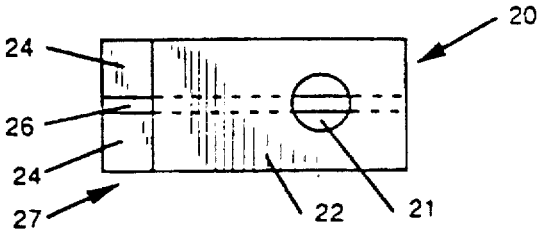
FIG. 2 is a plan view of the sampling cell of the present invention.
Figure 3:
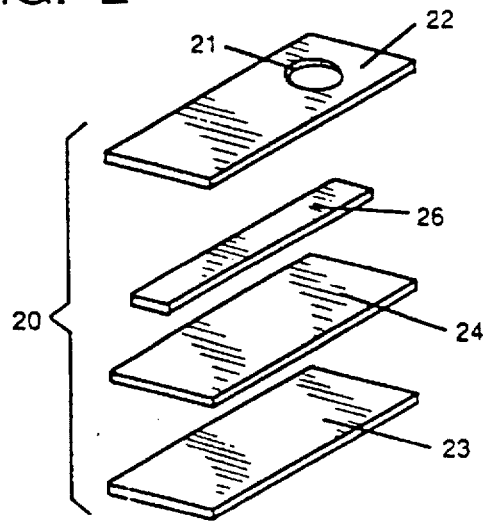
FIG. 3 is an exploded view of the sample cell shown in FIG. 2.

With reference to FIGS. 2 and 3, sample cell 20 is a metallized plastic substrate having a specifically-sized opening 21 which defines a volumetric well 21, when the cell is assembled, for containing a reagent pad and the blood to be analyzed. Cell 20 comprises a first substrate 22 and a second substrate 23 which may be preferably made from styrene or other substantially non-conducting plastic. Positioned on second substrate 23 is reference electrode 24. Reference electrode 24 may be preferably manufactured, for example, by vapor depositing the electrode onto a substrate made from a material such as the polyimide Kapton. In the preferred embodiment, reference electrode 24 is a silver-silver chloride electrode. This electrode can be produced by [first] depositing a silver *chloride* layer on a silver [chloride] layer by either chemical or electrochemical means before the substrate is used to construct the cells. The silver chloride layer may even be generated in-situ on a silver electrode when the reagent layer contains certain of the oxidants, such as ferricyanide, and chloride as shown in the following reactions:

$$Ag+Ox \rightarrow ag^{+}+Red$$

$$Ag^{+}+Cl^{-} \rightarrow AgCl.$$

Alternatively the silver-silver chloride electrode can be produced by depositing a layer of silver oxide (by reactive sputtering) onto the silver film. The silver oxide layer is then converted in-situ at the time of testing to silver chloride according to the reaction:

$$Ag_2O+H_2O+2Cl^{-} \rightarrow 2AgCl+2(OH)^{-}$$

when the sensor is wetted by the sample fluid and reconstitutes the chloride containing reagent layer. The silver electrode is thus coated with a layer containing silver chloride.

The reference electrode may also be of the type generally known as a "pseudo" reference electrode which relies upon the large excess of the oxidizing species to establish a known potential at a noble metal electrode. In a preferred embodiment, two electrodes of the same noble metal are used, however one is generally of greater surface area and is used as the reference electrode. The large excess of the oxidized species and the larger surface area of the reference resists a shift of the potential of the reference electrode.

Indicator or working electrode 26 can be either a strip of platinum, gold, or palladium metallized plastic positioned on reference electrode 24 or alternately the working electrode 26 and the reference electrode may be manufactured as a coplanar unit with electrode 26 being sandwiched between coplanar electrode 24 material. Preferable, sample cell 20 is prepared by sandwiching or laminating the electrodes between the substrate to form a composite unit.

As shown in FIG. 2, first substrate 22 is of a slightly shorter length so as to expose an end portion 27 of electrodes 24 and 26 and allow for electrical contact with the testing circuit contained in the apparatus. In this embodiment, after a sample has been positioned within well 21, cell 20 is pushed into window 19 of the front panel to initiate testing. In this embodiment, a reagent may be applied to well 21, or, preferably, a pad of dry reagent is positioned therein and a sample (drop) of blood is placed into the well 21 containing the reagent.

Figure 4:
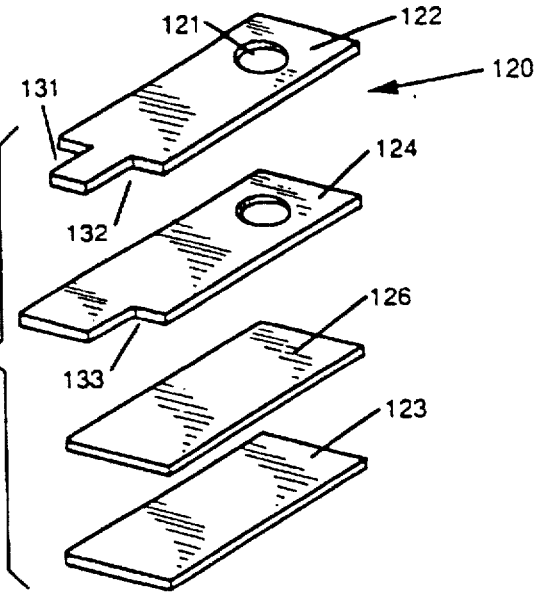
FIG. 4 is an exploded view of another embodiment of a sample cell according to the invention.
Figure 5:
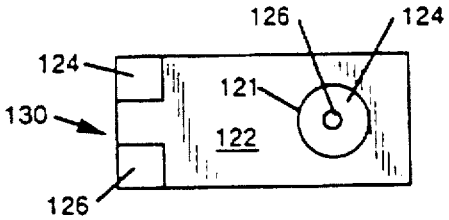
FIG. 5 is a plan view of the cell shown in FIG. 4.
Figure 6:
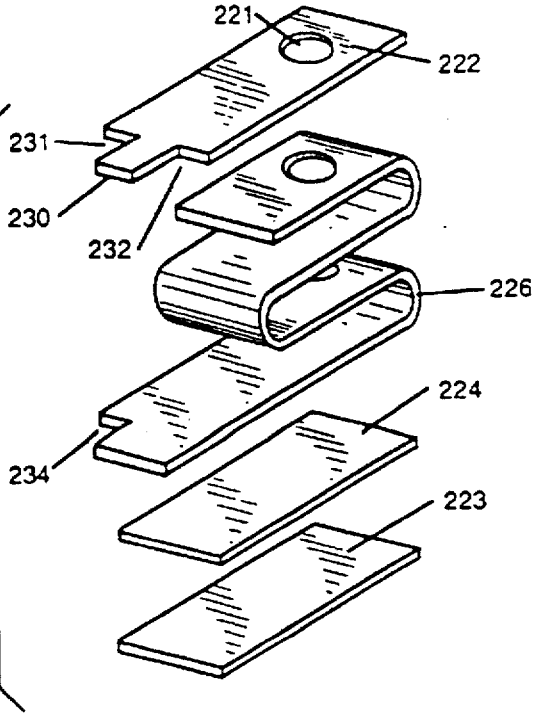
FIG. 6 is still another embodiment of a sample cell.

Referring to FIGS. 4–6, alternative embodiments of sample cell 20 are shown. In FIG. 4, sample cell 120 is shown having first 122 and second 123 substrates. Reference electrode 124 and working electrode 126 are laminated between substrates 122 and 123. Opening 121 is dimensioned to contain the sample for testing. End 130 (FIG. 5) is designed to be inserted into the apparatus, and electrical contact is made with the respective electrodes through cut-outs 131 and 132 on the cell. Reference electrode 124 also includes cut out 133 to permit electrical contact with working electrode 126.

In FIG. 6, working electrode 226 is folded, thereby providing increased surface area around opening 221, to achieve increased sensitivity or specificity. In this case, reference electrode 224 is positioned beneath working electrode 226. Working electrode includes cut out 234 to permit electrical contact with reference electrode 224 through cut out 231 in substrate 222. End 230 of substrate 222 also includes cut out 232 to permit electrical contact with working electrode 226.

Referring to FIGS. 1 and 2, the sample cell according to the present invention is positioned through window 19 (FIG. 1) to initiate the testing procedure. Once inserted, a potential is applied at portion 27 (FIG. 2) of the sample cell across electrodes 24 and 26 to detect the presence of the sample. Once the sample's presence is detected, the potential is removed and the incubation period initiated. Optionally during this period, a vibrator means 31 (FIG. 1) may be activated to provide agitation of the reagents in order to enhance dissolution (an incubation period of 20 to 45 seconds is conveniently used for the determination of glucose and no vibration is normally required). An electrical potential is next applied at portion 27 of the sample cell to electrodes 24 and 26 and the current through the sample is measured and displayed on display 16.

[The] *To* fully take advantage of the above apparatus, the needed chemistry for the sell testing systems is incorporated into a dry reagent layer that is positioned onto the disposable cell creating a complete sensor for the intended analyte. The disposable electrochemical cell is constructed by the lamination of metallized plastics and nonconducting materials in such a way that there is a precisely defined working electrode area. The reagent layer is either directly coated onto the cell or preferably incorporated (coated) into a supporting matrix such as filter paper, membrane filter, woven fabric or non-woven fabric, which is then placed into the cell. When a supporting matrix is used, it pore size and void volume can be adjusted to provide the desired precision and mechanical support. In general, membrane filters or nonwoven fabrics provide the best materials for the reagent layer support. Pore sizes of 0.45 to 50 μm and void volumes of 50–90% are appropriate. The coating formulation generally includes a binder such as gelatin, carrageenan, methylcellulose, polyvinyl alcohol, polyvinylpyrrolidone, etc., that acts to delay the dissolution of the reagents until the reagent layer has adsorbed most of the fluid from the sample. The concentration of the binder is generally on the order of 0.1 to 10% with 1–4% preferred.

The reagent layer imbibes a fixed amount of the sample fluid when it is applied to the surface of the layer thus eliminating any need for premeasurement of sample volume. Furthermore, by virtue of measuring current flow rather than reflected light, there is no need to remove the blood from the surface of the reagent layer prior to measurement as there is with reflectance spectroscopy systems. While the fluid sample could be applied directly to the surface of the reagent layer, to facilitate spread of blood across the entire surface of the reagent layer the sensor preferably includes a dispersing spreading or wicking layer. This layer, generally a non-woven fabric or adsorbant paper, is positioned over the reagent layer and acts to rapidly distribute the blood over the reagent layer. In some applications this dispersing layer could incorporate additional reagents.

For glucose determination, cells utilizing the coplanar design were constructed having the reagent layer containing the following formulations:

| | |
|---|---|
| Glucose oxidase | 600 u/ml |
| Potassium Ferricyanide | 0.4M |
| Phosphate Buffer | 0.1M |
| Potassium Chloride | 0.5M |
| Gelatin | 2.0 g/dl |

This was produced by coating a membrane filter with a solution of the above composition and air drying. The reagent layer was then cut into strips that just fit the window opening of the cells and these strips were place over the electrodes exposed within the windows. A wicking layer of a non-woven rayon fabric was then placed over this reagent layer and held in place with an overlay tape.

In order to prove the application of the technology according to the present invention, a large number of examples were run in aqueous solution at 25° C. The electrolyte consisted of a phosphate buffer of pH 6.8 which was about 0.1 molar total phosphate and 0.5M potassium chloride reagent. The potentials are referenced to a normal hydrogen electrode (NHE). In these tests it was found that any potential between approximately +0.8 and 1.2 volt (vs NHE) is suitable for the quantification of hydroquinone when benzoquinone is used as the oxidant. The limiting currents are proportional to hydroquinone concentrations in the range between 0.0001M and 0.050M.

Determination of glucose by Cottrell current ($i_r$) microchronoamperometry with the present method is created in the reaction of hydroquinone to benzoquinone. Cottrell currents decay with time in accordance with the equation:

$$i_r t^{1/2} = \text{const}$$

where t denotes time.

Figure 7:
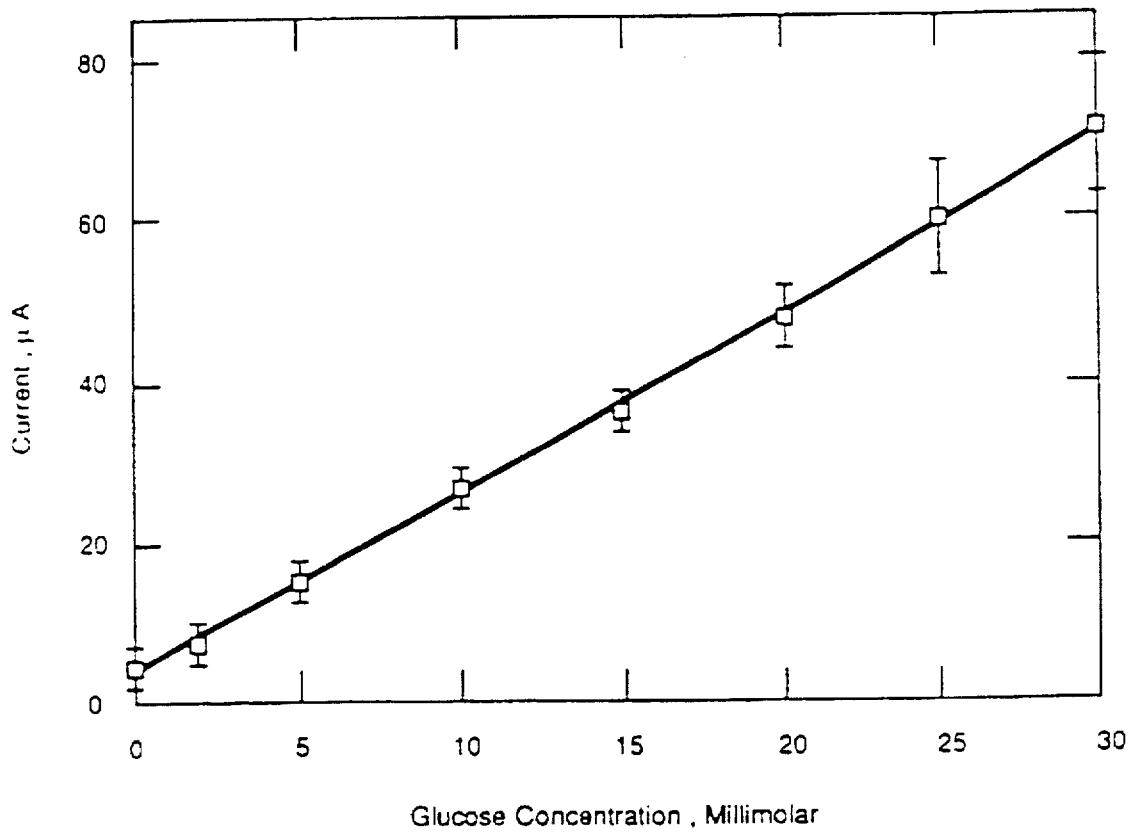
FIG. 7 is a graph showing current as a function of glucose concentration.
Figure 8:
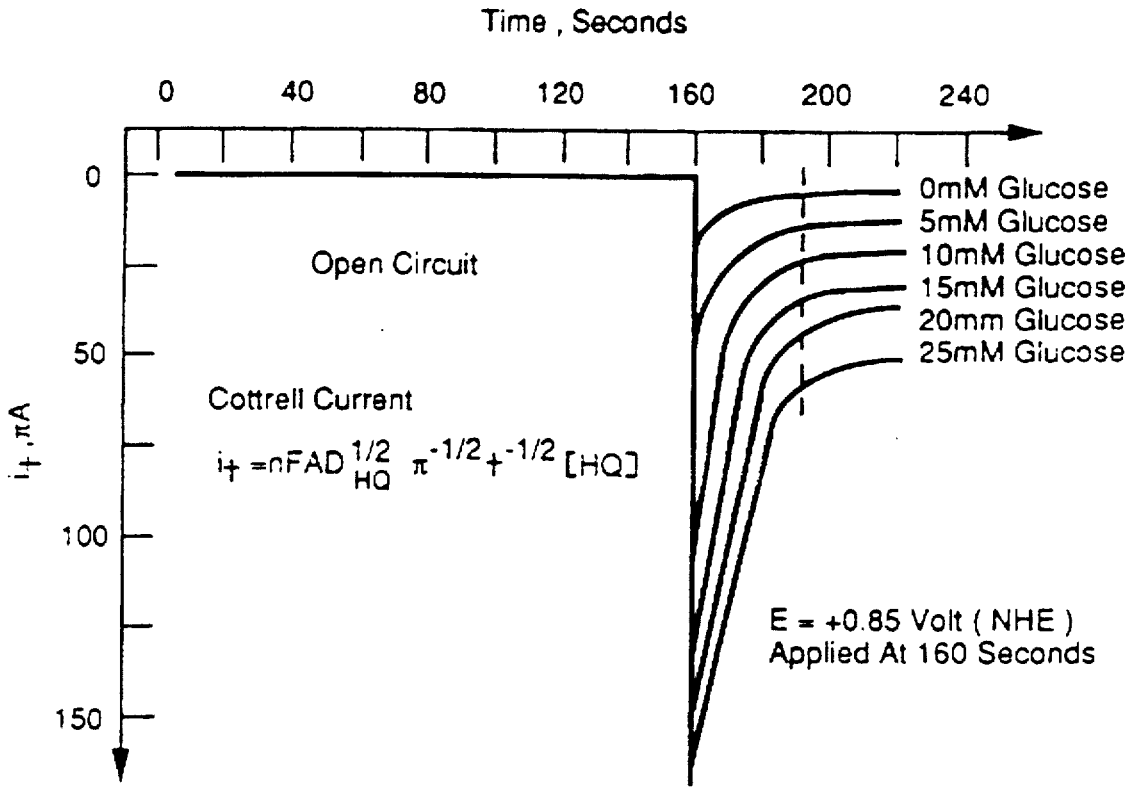
FIG. 8 is a graphical presentation of Cottrell current as a function of glucose concentration.

The main difference between these two techniques consists of applying the appropriate controlled potential after the glucose-benzoquinone reaction is complete and correlating glucose concentrations with Cottrell currents measured at a fixed time thereafter. The current-time readout is shown in FIG. 8. Proportionality between glucose concentrations and Cottrell currents (recorded at t=30 seconds after the application of potential) is shown in FIG. 7.

It should be noted that Cottrell chronoamperometry of metabolites needs the dual safeguards of enzymatic catalysis and controlled potential electrolysis. Gluconic acid yields of 99.9+ percent were attained in the presence of glucose oxidase. Concomitantly, equivalent amounts of benzoquinone were reduced to hydroquinone, which was conveniently quantitated in quiescent solutions, at stationary palladium thin film anodes or sample cells.

The results of these many tests demonstrates the microchronoamperometric methodology of the present invention and its practicality for glucose self-monitoring by diabetics.

In a presently preferred embodiment of the invention utilizing ferrocyanide, a number of tests were run showing certain improved operating capabilities.

Figure 9:
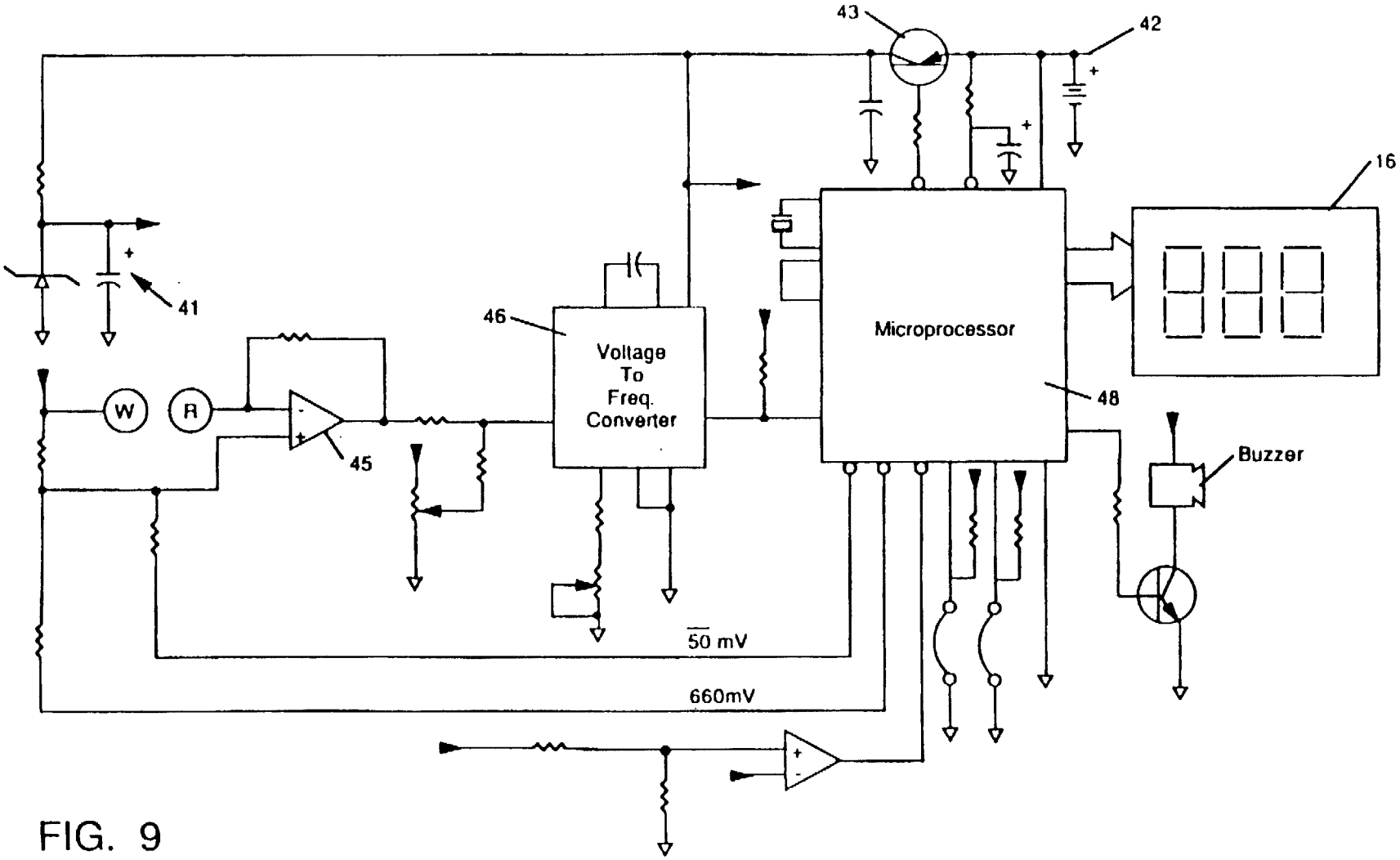
FIG. 9 is a presently preferred circuit diagram of an electrical circuit for use in the apparatus shown in FIG. 1.

Referring to FIG. 9, a schematic diagram of a preferred circuit 15 for use in the apparatus 10 is shown. Circuit 15 includes a microprocessor and LCD panel 16. The working and reference electrodes on the sample cell 20 make contact at contacts W (working electrode) and R (reference electrode), respectively. Voltage reference 41 is connected to battery 42 through analogue power switch 43. Current from the electrodes W and R is converted to a voltage by op amp 45. That voltage is converted into a digital signal (frequency) by and voltage to frequency converter 46 electrically connected to the microprocessor 48. The microprocessor 48 controls the timing of the signals. Measurement of current flow is converted by microprocessor 48 to equivalent glucose, cholesterol or other substance concentrations. Other circuits within the skills of a practiced engineer can obviously be utilized to obtain the advantages of the present invention.

Figure 10:
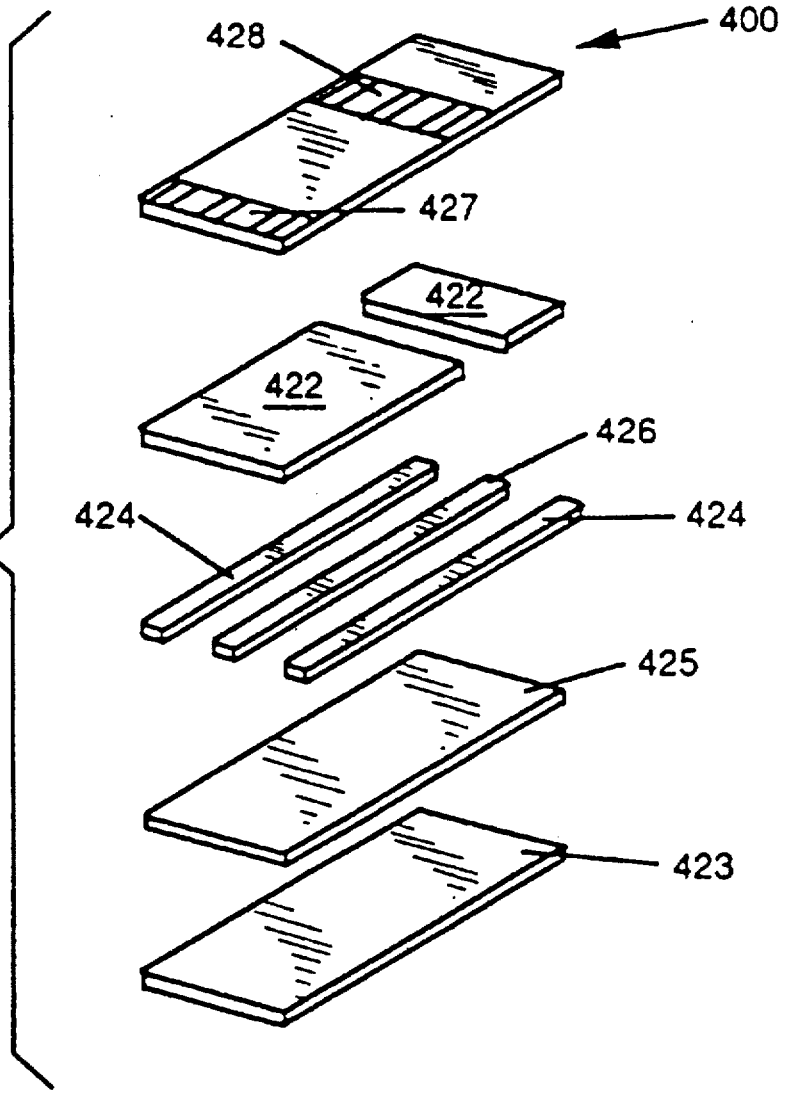
FIG. 10 is a preferred embodiment of the electrochemical cell.

With regard to FIG. 10, cell 400 consists of coplanar working 426 and reference 424 electrodes laminated between an upper 422 and lower 423 nonconducting material. Lamination is on an adhesive layer 425. The upper material 422 includes a die cut opening 428 which, along with the width of the working electrode material defines the working electrode area and provides (with an overlapping reagent layer not depicted) the sampling port of the cell. At one end of cell 400 is an open area 427 similar to end position 27 of FIG. 2.

The efficiency of using the apparatus according to the present invention to provide a means for in-home self testing by patients such as diabetics (in the preferred embodiment) can be seen in the following table in which the technology according to the present invention is compared to four commercially available units. As will be seen, the present invention is simpler, and in this instance simplicity breeds consistency in results.

GLUCOSE SYSTEM COMPARISONS

| Steps | 1 | 2 | 3 | 4 | Present Invention |
|---|---|---|---|---|---|
| Turn Instrument On | X | X | X | X | X |
| Calibrate Instrument | X | X | | | |
| Finger Puncture | X | X | X | X | X |
| Apply Blood | X | X | X | X | X |
| Initiate Timing Sequence | X | X | X | | |
| Blot | X | X | X | | |
| Insert Strip to Read | X | X | X | X | |
| Read Results | X | X | X | X | X |
| Total Steps Per Testing | 8 | 8 | 7 | 5 | 4 |
| Detection System | RS* | RS | RS | RS | Polarographic |
| Range (mg/dl) | 10–400 | 40–400 | 25–450 | 40–400 | 0–1000 |
| CV** | | | | | |
| Hypoglycemic | 15% | 15% | | | 5% |
| Euglycemic | 10% | 10% | | | 3% |
| Hyperglycemic | 5% | 5% | | | 2% |
| Correlation | 0.921 | 0.862 | | | 0.95 |

*RS—Reflectance Spectroscopy
**Coefficient of variation

With specific regard to the determination of cholesterol utilizing the present invention, the generalized chemistry may be depicted as:

Scheme I (1)

$$\text{Cholesterol Esters} + H_2O + CE \longrightarrow \text{Cholesterol} + \text{Fatty acid}$$

(2)

$$\text{Cholesterol} + OX + CO \longrightarrow \text{Cholestenone} + \text{Red}$$

(3)

$$\text{Red} \longrightarrow Ox + e^-$$

where the enzymes cholesterol esterase (CE) and cholesterol oxidase (CO) catalyze reactions 1 and 2 respectively and CO permits electron transfer with a variety of electroactive couples (Ox and Red). Reaction 2 is novel in that electron acceptors other than dioxygen may be used to oxidize cholesterol in the presence of the enzyme cholesterol oxidase. Reaction 1 is well known to those in the field and is necessary for the determination of total cholesterol (free cholesterol and cholesterol esters). Reaction 3 is an electro-oxidation process for probing and quantitating the cholesterol.

Utilizing alternative oxidants according to the present invention, the specific reactions become:

A:

$$\text{Cholesterol} + \text{2Ferricyanide-CO} \xrightarrow{\text{Reaction I above}} \text{Cholestenone} + \text{2Ferrocyanide}$$

$$\text{Ferrocyanide} \longrightarrow \text{Ferricyanide} + 1e^-$$

-continued

B:

$$\text{Cholesterol} + \text{Benzoquinone-CO} \xrightarrow{\text{Reaction 1 above}} \text{Cholestenone} + \text{Hydroquinone}$$

$$\text{Hydroquinone} \longrightarrow \text{Benzoquinone} + 2H^+ + 2e^-$$

Cholesterol oxidase (CO) from a variety of sources will catalyze electron transfer from cholesterol to a variety of the oxidants including benzoquinone, benzoquinone derivatives such as methylbenzoquinone, ethylbenzoquinone, chlorobenzoquinone, ortho-benzoquinone (oxidized form of catechol), benzoquinonesulfonate, and potassium ferricyanide. It is also anticipated that the enzyme will allow electron transfer with other alternate oxidants. As indicated in Reaction 3, the reduced product can then be monitored amperometrically for the quantitative determination of cholesterol.

Sources of the enzyme catalyzing the oxidation of cholesterol with alternate oxidants include CO from Nocardia, Streptomyces, Schizophyllum, Pseudomonas, and Brevibacterium; experimental conditions under which it is able to rapidly catalyze the oxidation of cholesterol by benzoquinone or any of the other oxidants depend somewhat upon the source of the enzyme. For example, CO from Streptomyces rapidly catalyzes substrate oxidation with benzoquinone in phosphate buffer in the presence of any of a variety of the surfactants including octylgluconopyranoside and CHAPSO; the same reaction under identical conditions with CO from either Brevibacterium or Nocardia is slower. However, both Nocardia and Brevibacterium sources are active catalysts for cholesterol oxidation by alternate oxidants under other conditions.

The oxidant also plays a role in which the enzyme is most active. For example, cholesterol oxidase from Nocardia rapidly catalyzes substrate oxidation with benzoquinone in 0.2 molar TRIS buffer and 3 g/dL CHAPSO but is slower with ferricyanide under identical conditions; the Brevibacterium source of the enzyme is relatively inactive with ferricyanide in TRIS buffer with a variety of surfactants but when benzoquinone is used as the oxidant the reaction is very fast. Alternatively, the Schizophyllum source of the enzyme CO rapidly catalyzes the oxidation of cholesterol in phosphate buffer with either ferricyanide or benzoquinone and with a variety of surfactants as activators.

As indicated, cholesterol oxidase will catalyze the oxidation of cholesterol by ferricyanide. Additional examples where CO catalyzes cholesterol oxidation by ferricyanide include a Nocardia source in TRIS buffer with a variety of surfactants including sodium deoxycholate, sodium taurodeoxycholate, CHAPS, Thesit, and CHAPSO. Furthermore, CO from Nocardia will also catalyze substrate oxidation with ferricyanide in phosphate buffer with sodium dioctylsulfosuccinate, sodium deoxycholate, sodium taurodeoxycholate, and Triton X-100. The buffer concentration is from 0.1 to 0.4 molar. Surfactant concentration for maximum activity of the oxidase enzyme varies with each detergent. For example, with deoxycholate or taurodeoxycholate, the enzyme in 0.2M TRIS is most active with detergent in the range from 20 to 90 millimolar. However, enzyme catalytic activity is observed up to [an] *and* through a 10% concentration. With octylgluconopyranoside, the maximum activity of the enzyme with the oxidant ferricyanide occurs at a detergent concentration of approximately 1.2%; however, the enzyme still maintains activity at higher and lower concentrations of the surfactant.

Both esterase and CO require a surfactant for high activity. Specific surfactants include sodium deoxycholate, sodium taurodeoxycholate, sodium glycodeoxycholate, CHAPS (3-(3-chlolamidopropyl)dimethylammonio-1-propanesulfonate), CHAPSO (3-(3-chlolamidopropyl) dimethylammonio-2-hydroxy-1-propanesulfonate), octylgluconopyranoside, octylthio-gluconopyranoside, nonylgluconopyranoside, dodecyl-gluconopyranoside, Triton X-100, Dioctyl sulfosuccinate, Thesit (Hydroxypolyethoxydodecane), and lecithin (phosphatidylcholine). Buffers acceptable for this reaction to occur with the enzyme include phosphate, TRIS, MOPS, MES, HEPES, Tricine, Bicine, ACES, CAPS, and TAPS. An alternate generallized reaction scheme for the measurement of cholesterol in serum and other biological fluids is given Scheme II

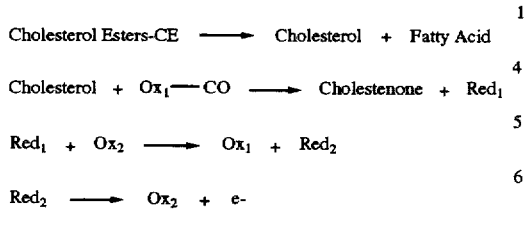

where Ox, and $Red_2$ function as an electron mediator couple between the cholesterol and the electroactive couple $Ox_2$/$Red_2$. In this case $Ox_1$ and $Red_1$ need not be electroactive because they do not have to participate in the electrooxidation process (Reaction 6). However, from both a thermodynamic and kinetic perspective, this couple with the assistance of the enzyme cholesterol oxidase must be able to accept electrons from cholesterol and relay them to the electroactive couple ($Ox_2$/$Red_2$). Specific examples of this chemistry include

EXAMPLE 1

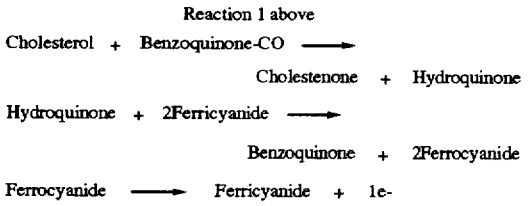

Scheme II is beneficial when the rate of reaction of cholesterol with the electroactive oxidant as in Scheme I is so slow that it precludes its use in a practical sensor. As mentioned above, Scheme II is also beneficial when the electron mediator itself ($Ox_1$/$Red_1$) is either not electroactive or exhibits poor electrochemistry under conditions of the enzyme chemistry. It is under these conditions that Scheme II is particularly applicable. Other electron mediators ($Ox_1$/$Red_1$) between cholesterol and ferricyanide for use in Scheme II may be possible including phenazine ethosulfate, phenazine methosulfate, tetramethylbenzidine, derivatives of benzoquinone, naphthoquinone and naphthoquinone derivatives, anthraquinone and anthraquinone derivatives, catechol, phenylenediamine, [tetramethylphenenediamine] *tetramethylphenylenediamine*, and other derivatives of phenylenediamine.

Furthermore, while it is understood that the oxidized form of the electron relay accepts electrons from cholesterol, in the sensor either the oxidized or the reduced form of the mediator may be incorporated provided it reacts rapidly with both cholesterol and ferricyanide. If the reduced form is sufficiently stable and the oxidized form is not, then reductant, may be incorporated into the sensor in relatively small quantity (in comparison with the analyte to be determined) and still provide the electron relay. However, this causes a corresponding background signal that must be accounted for. The reductant, must also be isolated from ferricyanide in the sensor by incorporation into a separate reagent layer.

Several formulations of the above chemistries encompassing both Schemes I and II have been prepare as dry films on membranes. These membranes are positioned in the sensor which can then be used for the determination of cholesterol. A preferred formulation of the reagents involving Scheme II consists of the following Cholesterol Esterase @400 Units/mL
Cholesterol Oxidase from Streptomyces @200 Units/mL
0.05 molar Potassium Ferricyanide
0.5 molar Potassium Chloride
0.2 molar Phosphate, pH 6.9
3 g/dL CHAPSO
2 g/dL gelatin
and 0.0001 molar hydroquinone (in the spreading or wicking layer).

The concentractions provided are [that] *those* of the solutions which are coated onto porous supports, filter paper or membranes; [these] *those* concentrations are reestablished when the membrane imbibes the serum or whole blood specimen. For cholesterol determinations large pore sizes in the filter support are *more* necessary than that used for glucose. This is because the cholesterol resides in the serum in large lipoproteins (chylomicrons[.] , LDL, VLDL, and HDL) which must penetrate the various layers of the sensor until they reach the reagents. The surfactants to the major extent break these natural micelles up into smaller micelles providing a greater total surface [are] *area* on which the enzymes catalyze the reaction. Due to the instability of benzoquinone, a small quantity of hydroquinone, which is more stable by nature of its lower vapor pressure, is incorporated into the sensor to assist electron mediation between cholesterol and ferricyanide. Upon introduction of the serum specimen into the sensor, the hydroquinone is oxidized to benzoquinone; the benzoquinone is then free to pick up electrons from the substrate and cycle them to ferricyanide. Under these conditions the rate of the reaction of cholesterol with a small quantity of benzoquinone is more rapid than that with a large excess of ferricyanide.

An alternate and preferred formulation of reagents utilizing Scheme II that may be incorporated into the reagent layer of the sensor is:

Cholesterol Oxidase from Streptomyces @200 Units/mL
Lipase from Candida @500 Units/mL
3 g/dL CHAPSO
0.2 molar TRIS, pH 7.5
0.05 molar Potassium Ferricyanide
0.5 molar Potassium Chloride
0.05 molar $MgCl_2$
2 g/dL gelatin
and 0.001 molar hydroquinone (in the spreading layer).

The magnesium salt in this formulation increases stability of the esterase enzyme in the phosphate-free reagent layer; Lipase assists the break up of the lipoproteins. With these dry reagent layers incorporated into the sensor and using the evaluation methodology as described, the following results were obtained.

| Serum Cholesterol, mg % | Average Current, uA |
|---|---|
| 91 | 19.3 |
| 182 | 27.2 |
| 309 | 38.5 |

These results demonstrate the quantitative response of the sensor to serum cholesterol levels.

Alternate and preferred embodiment of the sensor utilizing Scheme I is provided by reagent compositions:

Cholesterol Esterase @400 Units/mL

Cholesterol Oxidase from Nocardia @200 Units/mL 1 g/dL Triton X-100

0.1 molar TRIS buffer, pH 8.6

0.2 molar Potassium Ferricyanide 0.5 molar Potassium Chloride 0.02 molar $MgCl_2$ 2 g/dL gelatin

OR

Cholesterol Esterase @200 Units/mL

Cholesterol Oxidase from Streptomyces @200 Units/mL 0.06 molar Sodium deoxycholate 0.1 molar TRIS buffer, pH 8.6

0.2 molar Potassium Ferricyanide 0.5 molar Potassium Chloride 2 g/dL gelatin.

Thus, while we have illustrated and described the preferred embodiment of my invention, it is to be understood that this invention is capable of variation and modification, and we therefore do not wish or intend to be limited to the precise terms set forth, but desire and intend to avail ourselves of such changes and alterations which may be made for adapting the invention of the present invention to various usages and conditions. Accordingly, such changes and alterations are properly intended to be within the full range of equivalents, and therefore within the purview, of the following claims. The terms and expressions which have been employed in the foregoing specifications are used therein as terms of description and not of limitation, and thus there is no intention, in the use of such terms and expressions, of excluding equivalents of the features shown and described or portions thereof, it being recognized that the scope of the invention is defined and limited only by the claims which follow.

Having thus described our invention and the manner and process of making and using it in such full, clear, concise, and exact terms so as to enable any person skilled in the art to which it pertains, or to with which it is most nearly connected, to make and use the same.

We claim:

1. A method of measuring the amount of a selected compound in body fluids comprising, a) providing a measuring cell having at least a first and second electrode and said cell containing an oxidant and a buffer, b) placing a sample of fluid to be tested in said cell, c) reconstituting said oxidant and buffer with said sample fluid to generate a predetermined reaction, d) allowing said reaction to proceed substantially to completion, e) applying a potential across said electrodes and sample, and f) measuring the resulting Cottrell current to determine the concentration of said selected compound present in said sample.

2. A method as set forth in claim 1, wherein the compound is selected from the group consisting of glucose, cholesterol, TSH, T4, hormones, antiarrhythmics, antiepileptics and nontherapeutic drugs.

3. A method as set forth in claim 1, wherein the oxidant is a material selected from the group consisting of benzoquinone, ferricyanide, ferricinium, *orthophenanthroline* and Cobalt (III) dipyridyl.

4. The method as set forth in claim 1 including providing as said first electrode a working electrode and as said second electrode a reference electrode.

5. The method of claim 1 including also providing in said cell [and] *an* enzyme as a catalyst and said enzyme is an oxidoreductase.

6. The method of claim 1 including selecting said buffer from the group consisting of phosphate, TRIS, MOPS, MES, HEPES, Tricine, Bicine, ACES, CAPS and TAPS.

[7. A method for measuring the amount of glucose in blood, comprising a) providing a measuring cell having at least a first and second electrode and said cell containing an oxidant, a buffer and an enzyme, b) placing a blood sample to be tested in said cell, c) reconstituting said oxidant, buffer and enzyme with said blood sample to generate a predetermined reaction, d) essentially immediately applying a potential across said electrodes and blood sample, and e) measuring the resultant Cottrell current when the reaction has proceeded to completion to determine the concentration of said glucose present in blood sample.]

[8. The method of claim 7 including selecting said oxidant from the group consisting of benzoquinone, ferricyanide, ferricinium, Cobalt (III) orthophenantroline, and Cobalt (III) dipyridyl.]

[9. The method of claim 7 including providing as said first electrode a working electrode and said second electrode a reference electrode.]

[10. The method of claim 7 including adding as said enzyme, glucose oxydase.]

11. The method of claim 1 wherein *the sample of fluid is blood and* in step b) said placing of the blood sample to be tested in the cell generates a current and initiates a timing sequence, and wherein the reaction of step d) is allowed to proceed with an open circuit between said first and second [electrode] *electrodes.*

*12. A method of measuring the amount of an analyte in a blood sample, comprising:*

*a) adding the blood sample to an electrochemical cell that includes an electron transfer agent that will react in a reaction involving the analyte, thereby forming a detectable species;*

*b) incubating the reaction involving analyte and electron transfer agent in an open circuit until the reaction has substantially completed;*

*c) applying a sufficient potential difference between the electrodes of the electrochemical cell, after the incubation step, to readily transfer at least one electron between the detectable species and one of the electrodes, thereby resulting in a Cottrell current;*

*d) measuring the Cottrell current; and* e) correlating the measured Cottrell current to the amount of analyte in the blood sample.

13. The method of claim 12, wherein adding the blood sample to the electrochemical cell causes a sudden charging current, which automatically initiates incubation step b) performed under open circuit.

14. The method of claim 13, wherein the Cottrell current is measured at a preset time following the incubation step.

15. The method of claim 12, wherein the electrochemical cell further includes a catalyst in sufficient amount to catalyze the reaction involving the analyte and the electron transfer agent.

16. The method of claim 15, wherein the catalyst is an enzyme.

17. The method of claim 16, wherein the analyte is glucose and the enzyme is glucose oxidase.

18. The method of claim 12, wherein the electron transfer agent is included in a reagent layer that is coated directly onto the electrochemical cell or is incorporated into a supporting matrix that is placed into the electrochemical cell.

19. The method of claim 18, wherein the supporting matrix is filter paper, membrane filter, woven fabric, or nonwoven fabric.

20. The method of claim 18, wherein the reagent layer further includes a binder.

21. The method of claim 20, wherein the binder is gelatin, carrageenan, methylcellulose, polyvinyl alcohol, or polyvinylpyrrolidone.

22. The method of claim 21, wherein a dispersing, spreading, or wicking layer overlays the reagent layer.

23. The method of claim 18, wherein adding the blood sample to the electrochemical cell causes a sudden charging current, which automatically initiates incubation step b) performed under open circuit.

24. The method of claim 23, wherein the Cottrell current is measured at a preset time following the incubation step.

25. The method of claim 24, wherein the reagent layer further includes an enzyme catalyst in sufficient amount to catalyze the reaction involving the analyte and the electron transfer agent.

26. The method of claim 25, wherein the analyte is glucose in a concentration from about 1 milligram glucose per deciliter of blood sample to about 1000 milligrams glucose per deciliter of blood sample, and the fluid sample is blood.

27. The method of claim 26, wherein the electron transfer agent is ferricyanide, ferricinium, cobalt (III) orthophenanthroline, cobalt (III) dipyridyl, or benzoquinone.

28. The method of claim 12, wherein the analyte is glucose, TSH, $T_4$, a hormone, a cardiac glycoside, an antiarrhythmic, an antiepileptic, an antibiotic, cholesterol, or a non-therapeutic drug.

29. The method of claim 25, wherein the analyte is glucose in a concentration from about 1 milligram glucose per deciliter of blood sample to about 1000 milligrams glucose per deciliter of blood sample, the incubation period is from about 15 seconds to about 160 seconds, and current measurements are made in the range from about 2 seconds to about 30 seconds following the incubation step.

30. A method of measuring the amount of an analyte in a blood sample, comprising:

a) adding the blood sample to an electrochemical cell that includes an electron transfer agent, a first catalyst in sufficient amount to catalyze a first reaction involving the analyte, and a second catalyst in sufficient amount to catalyze a second reaction involving a product of the first reaction and the electron transfer agent, thereby forming a detectable species;

b) incubating the first and second reactions in an open circuit until the reactions have substantially completed;

c) applying a sufficient potential difference between electrodes of the electrochemical cell, after the incubation step, to readily transfer at least one electron between the detectable species and one of the electrodes, thereby resulting in a Cottrell current;

d) measuring the Cottrell current; and e) correlating the measured Cottrell current to the amount of analyte in the blood sample.

31. The method of claim 30, wherein adding the blood sample to the electrochemical cell causes a sudden charging current, which automatically initiates incubation step b) performed under open circuit.

32. The method of claim 31, wherein the Cottrell current is measured at a preset time following the incubation step.

33. A method of measuring the amount of cholesterol in a blood sample, comprising:

a) adding the blood sample to an electrochemical cell that includes an electron transfer agent, cholesterol esterase in sufficient amount to catalyze the hydrolysis of cholesterol esters in the blood sample, thereby forming cholesterol, cholesterol oxidase in sufficient amount to catalyze a reaction involving cholesterol and the electron transfer agent, thereby forming a detectable species;

b) incubating the reactions of step a) in an open circuit until those reactions have substantially completed;

c) applying a sufficient potential difference between electrodes of the electrochemical cell, after the incubation step, to readily transfer at least one electron between the detectable species and one of the electrodes, thereby resulting in a Cottrell current;

d) measuring the Cottrell current; and e) correlating the measured Cottrell current to the amount of cholesterol in the blood sample.

34. The method of claim 33, wherein adding the blood sample to the electrochemical cell causes a sudden charging current, which automatically initiates incubation step b) performed under open circuit.

35. The method of claim 34, wherein the Cottrell current is measured at a preset time following the incubation step.

36. The method of claim 35, wherein the electron transfer agent is ferricyanide or benzoquinone.

37. A method of measuring the amount of an analyte in a blood sample, comprising:

a) adding the blood sample to an electrochemical cell that includes first and second electron transfer agents, a first catalyst in sufficient amount to catalyze a first reaction involving the analyte, a second catalyst in sufficient amount to catalyze a second reaction involving a product of the first reaction and the first electron transfer agent, thereby forming an intermediate species that reacts with the second electron transfer agent, thereby forming a detectable species;

b) incubating the reactions of step a) in an open circuit until those reactions have substantially completed;

c) applying a sufficient potential difference between electrodes of the electrochemical cell, after the incubation

*step, to readily transfer at least one electron between the detectable species and one of the electrodes, thereby resulting in a Cottrell current;*

*d) measuring the Cottrell current; and*

*e) correlating the measured Cottrell current to the amount of analyte in the blood sample.*

*38. A method of measuring the amount of cholesterol in a blood sample, comprising:*

*a) adding the blood sample to an electrochemical cell that includes*

*first and second electron transfer agents,*

*cholesterol esterase in sufficient amount to catalyze the hydrolysis of cholesterol esters in the blood sample, thereby forming cholesterol,*

*cholesterol oxidase in sufficient amount to catalyze a reaction involving cholesterol and the first electron transfer agent, thereby forming an intermediate species that reacts with the second electron transfer agent, thereby forming a detectable species;*

*b) incubating the reactions of step a) in an open circuit until those reactions have substantially completed;*

*c) applying a sufficient potential difference between the electrodes of the electrochemical cell, after the incubation step, to readily transfer at least one electron between the detectable species and one of the electrodes, thereby resulting in a Cottrell current;*

*d) measuring the Cottrell current; and*

*e) correlating the measured Cottrell current to the amount of cholesterol in the blood sample.*

*39. The method of claim 38, wherein adding the blood sample to the electrochemical cell causes a sudden charging current, which automatically initiates incubation step b) performed under open circuit.*

*40. The method of claim 39, wherein the Cottrell current is measured at a preset time following the incubation step.*

*41. The method of claim 40, wherein the first electron transfer agent is benzoquinone, phenazine ethosulfate, phenazine methosulfate, tetramethylbenzidine, a derivative of benzoquinone, naphthoquinone, a derivative of naphthoquinone, anthraquinone, a derivative of anthraquinone, catechol, phenylenediamine, tetramethylphenylenediamine, or a derivative of phenylenediamine.*

*42. The method of claim 41, wherein the second electron transfer agent is ferricyanide.*

*43. A method for measuring the amount of a selected compound in a blood sample, comprising:*

*providing a measuring cell having at least first and second electrodes for contact with the blood sample introduced into the cell,*

*applying a potential to the electrodes to detect the presence of the blood sample in the cell,*

*placing the blood sample into the cell,*

*removing the potential to the electrodes after the blood sample is detected in the cell,*

*selectively oxidizing the compound in the blood sample with an oxidized electron acceptor to produce an oxidized form of the selected compound and a reduced electron acceptor, and*

*re-applying a potential across the cell electrodes after the selective oxidation of the compound in the blood sample has substantially completed and measuring the resulting Cottrell current, said current being proportional to the concentration of the reduced electron acceptor and the selected compound in the blood sample.*

*44. The method of claim 43, wherein placing the fluid sample into the measuring cell causes a sudden charging current, which automatically initiates removal of the potential from the electrodes and performance of the selective oxidation of the selected compound under open circuit.*

*45. The method of claim 44, wherein the Cottrell current is measured at the preset time after re-application of a potential across the measuring cell electrodes.*

*46. The method of claim 47, wherein placing the volume of blood into the measuring cell causes a sudden charging current, which automatically initiates removal of the potential across the electrodes and performance of the oxidation of glucose in the blood under open circuit.*

*47. A method for measuring the amount of glucose in blood, comprising:*

*providing a measuring cell with at least first and second electrodes for contact with blood introduced into the cell,*

*applying a potential across the electrodes,*

*placing a volume of blood into the cell,*

*removing the potential across the electrodes after the volume of blood is placed into the measuring cell,*

*oxidizing the glucose in the blood with an oxidized electron acceptor in the presence of glucose oxidase to produce gluconic acid and a reduced electron acceptor,*

*re-applying a potential across the measuring cell electrodes after the oxidation of glucose has substantially completed, and*

*measuring the Cottrell current through the cell, the Cottrell current being proportional to the glucose concentration in the blood.*

*48. The method of claim 46, wherein the Cottrell current is measured at a preset time after re-application of a potential across the measuring cell electrodes.*

* * * * *